United States Patent
Hoffacker et al.

(10) Patent No.: US 8,361,169 B2
(45) Date of Patent: Jan. 29, 2013

(54) METHODS FOR FORMING DYED MICROSPHERES AND POPULATIONS OF DYED MICROSPHERES

(75) Inventors: Kurt D. Hoffacker, Austin, TX (US); Ananda G. Lugade, Austin, TX (US); Ewald Terpetschnig, Urbana, IL (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 13/246,486

(22) Filed: Sep. 27, 2011

(65) Prior Publication Data
US 2012/0035328 A1 Feb. 9, 2012

Related U.S. Application Data

(62) Division of application No. 11/247,942, filed on Oct. 11, 2005, now Pat. No. 8,038,734.

(60) Provisional application No. 60/618,340, filed on Oct. 12, 2004.

(51) Int. Cl.
C07C 247/00 (2006.01)
(52) U.S. Cl. ............... 8/506; 8/514; 8/694; 552/5
(58) Field of Classification Search ............. 8/506, 514, 8/694; 552/5
See application file for complete search history.

(56) References Cited

U.S. PATENT DOCUMENTS

| | | | | |
|---|---|---|---|---|
| 3,278,305 A | 10/1966 | Urbain et al. | | 430/306 |
| 3,278,306 A | 10/1966 | Greenhalgh | | 430/376 |
| 3,507,829 A | 4/1970 | Bostick et al. | | 525/390 |
| 3,674,480 A | 7/1972 | Kampfer et al. | | 430/196 |
| 3,695,821 A | 10/1972 | Kuroki et al. | | 8/444 |
| 3,887,379 A | 6/1975 | Clecak et al. | | 430/197 |
| 4,322,211 A | 3/1982 | Hoyle et al. | | 8/402 |
| 4,415,334 A | 11/1983 | Hoyle et al. | | 8/694 |
| 4,556,625 A | 12/1985 | Lenox et al. | | 430/145 |
| 4,613,559 A | 9/1986 | Ober et al. | | 430/137.17 |
| 5,580,697 A | 12/1996 | Keana et al. | | 430/296 |
| 5,582,955 A | 12/1996 | Keana et al. | | 430/296 |
| 5,587,273 A | 12/1996 | Yan et al. | | 430/296 |
| 5,981,180 A | 11/1999 | Chandler et al. | | 435/6.12 |
| 6,022,597 A | 2/2000 | Yan et al. | | 427/558 |
| 6,046,807 A | 4/2000 | Chandler | | 356/318 |
| 6,139,800 A | 10/2000 | Chandler | | 422/82.08 |
| 6,268,222 B1 | 7/2001 | Chandler et al. | | 436/523 |
| 6,350,618 B1 * | 2/2002 | Borrelli et al. | | 436/174 |
| 6,366,354 B1 | 4/2002 | Chandler | | 356/318 |
| 6,411,904 B1 | 6/2002 | Chandler | | 702/21 |
| 6,449,562 B1 | 9/2002 | Chandler et al. | | 702/19 |
| 6,514,295 B1 * | 2/2003 | Chandler et al. | | 8/607 |
| 6,524,793 B1 | 2/2003 | Chandler et al. | | 435/6.12 |
| 6,528,165 B2 | 3/2003 | Chandler et al. | | 428/402.2 |
| 6,599,331 B2 | 7/2003 | Chandler et al. | | 8/611 |
| 6,632,526 B1 | 10/2003 | Chandler et al. | | 428/402 |
| 6,649,414 B1 | 11/2003 | Chandler et al. | | 436/63 |
| 6,737,236 B1 | 5/2004 | Pieken et al. | | 435/5 |
| 2002/0096795 A1 | 7/2002 | Chandler | | 264/4.1 |
| 2003/0017164 A1 | 1/2003 | Rajagopalan et al. | | 424/178.1 |
| 2003/0028981 A1 | 2/2003 | Chandler et al. | | 8/607 |
| 2003/0073086 A1 | 4/2003 | Guire et al. | | 506/9 |
| 2004/0053052 A1 | 3/2004 | Chandler et al. | | 428/407 |

FOREIGN PATENT DOCUMENTS

| | | |
|---|---|---|
| GB | 1344991 | 1/1974 |
| GB | 1344992 | 1/1974 |
| GB | 1344993 | 1/1974 |
| GB | 1403996 | 9/1975 |
| GB | 1406996 | 9/1975 |
| GB | 1412963 | 11/1975 |
| JP | 2002-129060 | 5/2002 |
| WO | WO 99/37814 | 7/1999 |
| WO | WO 99/52708 | 10/1999 |
| WO | WO 01/51566 | 7/2001 |
| WO | WO 03/003806 | 1/2003 |
| WO | WO 03/095568 | 11/2003 |

OTHER PUBLICATIONS

Matsuo, In situ visualization of messenger RNA for basic fibroblast growth factor in living cells. Biochimica et Biophysica Acta 1379(1998) 178-184.*
Abramovitch et al., "Intramolecular insertion of arylsulfonylintrenes into aliphatic side chains," *J. Org. Chem.*, 42(17):2920-2926, 1977.
Abramovitch et al., "Thermal decomposition of o- and p-benzenedisulfonyl azides in benzene, cyclohexane, cyclohexene, and tetracyclone," *J. Org. Chem.*, 40(7):883-889, 1975.
Autrey et al., "Are aroyinitrenes ground-state singlets? Photochemistry of beta-naphthoyl azide," *J. Am. Chem.. Soc.*, 109:5814-5820, 1987.
Ayyangar et al., "Azides Part II —Mechanism of fixation of sulphoazido dyes on polyester fibre," *NCL Communication*, No. 2298, pp. 55-57, 1979.
Ayyangar et al., "Coloured particles by dispersion polymerization," *Eur. Polym. J..*, 23(8):617-622, 1987.
Ayyangar et al., "Reactive dyes containing the azido group of synthetic-polymer fibres," *JSDC*, pp. 13-19, 1979.

(Continued)

*Primary Examiner* — Lorna M Douyon
*Assistant Examiner* — Amina Khan
(74) *Attorney, Agent, or Firm* — Fulbright & Jaworski L.L.P.

(57) ABSTRACT

Various methods for forming dyed microspheres are provided. One method includes activating a chemical structure coupled to a dye using heat or light to form a reaction intermediate in the presence of a microsphere. The reaction intermediate covalently attaches to a polymer of the microsphere thereby coupling the dye to the polymer and forming the dyed microsphere. Additional methods are provided for forming a dyed microsphere coupled to a molecule. These methods include dyeing the microspheres as described above in addition to synthesizing the molecule on an outer surface of the dyed microspheres. A population of dyed microspheres is also provided. Each of the dyed microspheres of the population includes a dye attached to a polymer of each of the dyed microspheres by a chemical structure. A coefficient of variation in dye characteristics of the population of dyed microspheres attributable to the dye is less than about 10%.

15 Claims, 2 Drawing Sheets

OTHER PUBLICATIONS

Azides and Nitrenes, copyright 1984 Academic Press, Inc., pp. 491-521.

Cai et al., "Bis(perfluorophenyl) azides: Efficient cross-linking agents for deep-UV and electronic beam lithography," *Chem. Master.*, 2:631-633, 1990.

Enger et al., "Tagging in combinatorial chemistry: the use of coloured and fluorescent beads," *Chem. Commun.*, 8:735-736, 1997.

Griffiths et al, "Transfer-printing properties of sulphonyl- and aryl-azides dyes on nylon 6.6," *JSDC*, pp. 65-70, 1987.

Griffiths et al., "The mechanism of fixation of sulphonazide disperse dyes on nylon 6," *JSDC*, pp. 455-458, 1997.

Handbook of Fluorescent probes and Research Products, 9$^{th}$ Edition, copyright 2002 Molecular Probes, Inc., pp. 144-146.

Horak et al., "Preparation of colored poly(styrene-co-butyl methacrylate) micrometer size beads with narrow size distribution by dispersion polymerization in presence of dyes," *Journal of Polymer Science, Part A: Polymer Chemistry*, 33:2961-2968, 1995.

Karamancheva et al., "Thermal investigation of sulphonylazide dyes," *Dyes and Pigments*, 13:155-160, 1990.

Leffler et al., "Some decomposition reactions of acid azides," *J. Org. Chem.*, 28:902-906, 1962.

Liu and Yan, "Perfluorophenyl azides: new applications in surface functionalization and nanomaterial synthesis," *Accounts of Chemical Research*, 43(11):1434-1443, 2010.

Milligan et al., "The potential of azido-substituted dyes as latent reactive dyes for wool," *JSDC*, 352-256, 1978.

Modi et al., "Heteroyclic monoazo dyes derived from 4-oxoquinazoline: Part II," *Dyes and Pigments*, 23:25-32, 1993.

Nanthakumar et al., "Solid-phase oligonucleotide synthesis and flow cytometric analysis with microspheres encoded with covalently attached fluorphores," *Bioconjugate Chem.*, 11:282-288, 2000.

Office Communication issued in Chinese Patent Application No. 200580034419.8, dated Jan. 22, 2010. (English translation).

Office Communication issued in Chinese Patent Application No. 200580034419.8, dated Jul. 8, 2010. (English translation).

Office Communication issued in European Patent Application No. 05812255.7, dated Sep. 9, 2010.

Office Communication issued in Japanese Patent Application No. 2007-0536820, dated Nov. 2, 2010. (English translation).

Office Communication issued in Japanese Patent Application No. 2007-0536820, dated Sep. 6, 2011. (English translation).

Office Communication issued in U.S. Appl. No. 11/247,942, dated Dec. 10, 2010.

Office Communication issued in U.S. Appl. No. 11/247,942, dated Jul. 22, 2009.

Office Communication issued in U.S. Appl. No. 11/247,942, dated Oct. 20, 2008.

Office Communication issued in U.S. Appl. No. 11/247,942, dated Apr. 21, 2008.

Office Communication issued in Chinese Patent Application No. 200580034419.8, dated Apr. 25, 2011. (English translation).

Office Communication issued in Chinese Patent Application No. 200580034419.8, dated May 8, 2009. (English translation).

Office Communication, issued in Indian Patent Application No. 382/MUMNP/2007, dated Nov. 21, 2008.

PCT International Preliminary Report on Patentability issued in International Application No. PCT/US2005/036571, mailed Apr. 26, 2007.

PCT International Search Report issued in International Application No. PCT/US2005/036571, mailed Apr. 28, 2006.

Rieger, "The glass transition temperature of polystyrene," *Journal of Thermal Analysis*, 46:965-972, 1996.

Sebestyén et al., "Coloured peptides: Synthesis, properties and use in preparation of peptide sub-library kits," *Journal of Peptide Science*, 4:294-299, 1998.

Ulrich et al., "New syntheses of functional arenesulfonyl azides," *J. Org. Chemi.*, 40(6):802-804, 1975.

Winnik et al., "Coloured particles by dispersion polymerization," *Eur. Polym. J.*, 2398):617-622, 1987.

Yates et al., "Colored polymer microparticles through carbon dioxide-assisted dyeing," *Langmuir*, 16(11):4757-4760, 2000.

\* cited by examiner

METHODS FOR FORMING DYED MICROSPHERES AND POPULATIONS OF DYED MICROSPHERES This is a divisional of U.S. patent application Ser. No. 11/247,942, filed Oct. 11, 2005 now U.S. Pat. No. 8,038,734, which claims priority to U.S. Provisional Patent Application Ser. No. 60/618,340, filed Oct. 12, 2004. The above-referenced disclosures are incorporated herein by reference in their entirety.

PRIORITY CLAIM

This application claims priority to U.S. Provisional Application No. 60/618,340 entitled "Methods for Forming Dyed Microspheres and Populations of Dyed Microspheres," filed Oct. 12, 2004, which is incorporated by reference as if fully set forth herein.

BACKGROUND OF THE INVENTION

1. Field of the Invention

This invention generally relates to methods for forming dyed microspheres and populations of dyed microspheres. Certain embodiments include activating a chemical structure coupled to a dye using heat or light to form a reaction intermediate in the presence of a microsphere such that the reaction intermediate covalently attaches to a polymer of the microsphere thereby coupling the dye to the polymer.

2. Description of the Related Art

The following descriptions and examples are not admitted to be prior art by virtue of their inclusion within this section.

Spectroscopic techniques are widely employed in the analysis of chemical and biological systems. Most often, these techniques involve the absorption or emission of electromagnetic radiation by the material of interest. One such application is in the field of microarrays, which is a technology exploited by a large number of disciplines including the combinatorial chemistry and biological assay industries. One company, Luminex Corporation of Austin, Tex., has developed a system in which biological assays are performed on the surface of variously colored fluorescent microspheres. One example of such a system is illustrated in U.S. Pat. No. 5,981,180 to Chandler et al., which is incorporated by reference as if fully set forth herein. These microspheres are interrogated in a fluid flow device by laser excitation and fluorescence detection of each individual microsphere as they pass at relatively high speed through a detection zone. These values may be easily exported to a database for further analysis.

In the above-mentioned system, fluorescent dyes are absorbed into the microspheres and/or bound to the surface of the microspheres. The dyes are generally chosen based on their ability to emit light at the wavelength of the selected detection window. Further, the detection windows are spaced apart by a certain number of to wavelengths, and the dyes are typically designed to minimize the overlap of a dye's fluorescent signal within adjacent windows. In one example, by employing two detection windows and two dyes, each at 10 different concentrations, there would thus be 100 fluorescently distinguishable microsphere sets.

Conventional methods of dyeing microspheres by covalent and noncovalent reactions can be summarized as follows. For instance, dyed microspheres can be produced through dispersion polymerization by several methods. Dyes can be dissolved in the monomer prior to polymerization as described by Hovak, D. et al. in J. Polym. Sci., Part A, Polym. Chem., 33, 2961-2968, 1995, which is incorporated by reference as if fully set forth herein. Microspheres can also be dyed after polymerization using an organic solvent to swell the particles and transport the dye into the particles. Examples of such dyeing methods are illustrated in U.S. Pat. No. 4,613,559 to Ober, U.S. Pat. No. 6,514,295 to Chandler et al., U.S. Pat. No. 6,528,165 to Chandler et al., U.S. Pat. No. 6,599,331 to Chandler et al., U.S. Pat. No. 6,632,526 to Chandler et al., and U.S. Pat. No. 6,649,414 to Chandler et al., which are incorporated by reference as if fully set forth herein.

Copolymerization of reactive dyes may be employed to obtain particles with chemically bound dyes. Examples of such methods are described by Winnik, F. M. et al. in Eur. Polym. J., 23, 617-622, 1987, which is incorporated by reference as if fully set forth herein. Alternatively, the particles or microcarriers can be optically encoded by fluorescent dyes (or smaller dyed particles) that are covalently bound to their surfaces. Examples of such methods are described by Sebestyen F. et al. in J. Pept. Science, 4, 294-299, 1998, Egner, B. J. et al. in J. Chem. Soc. Chem. Commun., 8, 735-736, 1977, Manthakumar, A. et al. in Bioconj. Chem., 11, 282-292, 2000, and U.S. Pat. No. 6,268,222 to Chandler et al., all of which are incorporated by reference as if fully set forth herein.

C—H bond insertion by a carbene or nitrene moiety is a desirable pathway for establishing a stable covalent linkage between two organic molecules as described by to Breslow, R., Scriven (Ed.), Azides and Nitrenes, Chapter 10, AP, New York, 1984, which is incorporated by reference as if fully set forth herein. The use of nitrene as the reactive intermediate has stimulated efforts to develop new reagents which undergo C—H insertion efficiently as described by Autrey, R. et al. in J. Am. Chem. Soc., 109, 5814, 1987, which is incorporated by reference as if fully set forth herein. Perfluorophenyl azides (PFPA) have been shown to exhibit improved C—H insertion efficiency over their non-fluorinated analogs. Examples of such azides are illustrated in U.S. Pat. No. 5,580,697 to Keana et al., U.S. Pat. No. 5,582,955 to Keana et al., U.S. Pat. No. 5,587,273 to Keana et al., and U.S. Pat. No. 6,022,597 to Keana et al. and U.S. Patent Publication No. US 2003/0017164 to Rajagopalan et al., all of which are incorporated by reference as if fully set forth herein.

The methods described above, however, do have a number of drawbacks. For example, dissolving a dye in monomers prior to polymerization usually results in reduced conversion and polydisperse particles (a mixture of different sized particles) due to radical chain termination by the dye during polymerization. In addition, the usefulness of copolymerization of reactive dyes is limited by the lack of dyes that are stable under radical polymerization conditions. In particular, reactive dyes can change color during polymerization as described by Yates, M. Z. et al. in Langmuir, 16(11), 4757-4760, 2000, which is incorporated by reference as if fully set forth herein.

Accordingly, in view of the present state of the art in covalent coupling of dyes to microspheres for generating solvent-fast or organotolerant beads, there remains a need for a suitable method for covalent dyeing of microspheres.

Various molecules containing multiple azide groups have been used to crosslink polymers. Heat and light have been used to convert azide moieties to reactive nitrene groups. For example, conversion of carbonyl azide using light is described in U.S. Pat. No. 3,278,306 to Urbain et al., which is incorporated by reference as if fully set forth herein. Conversion of sulfonyl azide at 175° C. is described in U.S. Pat. No. 3,507,829 to Bostick et al., which is incorporated by reference as if fully set forth herein. Conversion of aromatic azide using light is described in U.S. Pat. No. 3,887,379 to Clecak et al., which is incorporated by reference as if fully set forth herein. Conversion of PFPA using light is described by Cai et al. in Chem. Mater., 2, 631, 1990, which is incorporated by reference as if fully set forth herein.

In the early 1970s, Kodak was assigned a series of patents for permanently dyeing hydrophobic polymers with various dyes (e.g., azo or quinone dyes) with appended sulfonyl azide moieties. The sulfonyl azide moiety was used to covalently attach dye molecules to a polymer substrate through the intermediate nitrene that is generated with heat or light. Unreacted dye molecules could be subsequently washed away. In particular, Great Britain Patent Nos. 1 344 991 to Holstead et al. and 1 344 992 to Holstead et al. describe the use of sulfonyl azide moieties attached directly to aromatic rings of various dyes and fluorescent brighteners. After heating or irradiation of dye-embedded-polymer (in the form of film or fiber), the dye forms a new bond with the polymer. Great Britain Patent No. 1 344 993 to Holstead et al. describes the use of similar reactive dyes as part of photographic materials. Great Britain Patent No. 1 406 996 to Shuttleworth describes the preparation of reactive dyes through the attachment of benzene sulfonic azide through a linker group to various dye molecules. Great Britain Patent No. 1 412 963 to Pullan describes the use of dyes with various reactive groups (including sulfonyl azide) in transfer printing onto fabrics or films. All of the Great Britain Patents described above are incorporated by reference as if fully set forth herein.

Other companies have patented the use of sulfonyl azide containing dyes for the fast dyeing of fibers and shape articles as described in U.S. Pat. No. 3,695,821 to Kuroki et al. and photographic dry copying as described in U.S. Pat. No. 3,674,480 to Kampfer et al., both of which are incorporated by reference as if fully set forth herein. Armstrong World Industries, Inc., Lancaster, Pa., received patents in the early 1980s relating to the use of sulfonyl azide containing compounds to impart permanent to yellow and brown colors to articles as described in U.S. Pat. No. 4,322,211 to Hoyle et al., U.S. Pat. No. 4,415,334 to Hoyle et al., and U.S. Pat. No. 4,556,625 to Lenox et al., all of which are incorporated by reference as if fully set forth herein. In addition, several academic groups have explored the use of sulfonyl azide groups for the fast dyeing of polymer fibers as described by Ayyangar, N. R. et al., in Journal of the Society of Dyers and Colorists (JSDC), pp. 13-19 and 55-57, 1979, Griffiths, J. et al., JSDC, pp. 455-458, 1977, Griffiths, J. et al., JSDC, pp. 65-70, 1978, Milligan, B. et al., JSDC, pp. 352-356, 1978, and Desai, K. R. et al., Dyes and Pigments, 23, pp. 25-32, 1993, which are incorporated by reference as if fully set forth herein.

The effect of substituents on the thermal decomposition of sulfonyl azides to nitrenes has been studied as described by Katamancheva, I. et al., Dyes and Pigments, 13, pp. 155-160, 1990, Ayyangar, N. R. et al., Indian J. of Chemistry, 30B, pp. 42-45, 1991, and Leffler, J. E. et al., J. Org. Chem., 28, pp. 902-906, 1963, which are incorporated by reference as if fully set forth herein. Studies into the basic mechanism of the sulfonyl azide reaction have also been reported as described by Abramovitch, R. A. et al., J. Org. Chem., 40, pp. 883-889, 1975, Abramovitch, R. A. et al., J. Org. Chem., 42, pp. 2920-2936, 1997, and Ulrich, J., J. Org. Chem., 40, pp. 802-804, 1975, which are incorporated by reference as if fully set forth herein.

Certain biological assays require the attachment of chemically synthesized biomolecules (e.g., oligonucleotides, peptides, or oligosaccharides). These biomolecules may be produced by automated synthesis on microsphere resins (non-dyed) in organic solvents. After synthesis, the biomolecules are cleaved from the support and then attached to dyed microspheres using aqueous methods. This process would be simpler and cheaper if the synthesis could be performed directly on dyed microspheres. However, currently used microspheres would exhibit a loss in dye if exposed to the organic solvents involved in the synthesis. Hence, "organotolerant" microspheres, or microspheres that would retain their fluorescent signatures even if exposed to organic solvents, are desired.

Methods have been developed to impart organotolerance to microspheres that would otherwise be organo-intolerant. For example, U.S. Pat. No. 6,528,165 to Chandler, which is incorporated by reference as if fully set forth herein, describes silicon and sugar based coatings that when formed on dyed microspheres could impart organotolerance to the dyed microspheres. In addition, other molecules (such as antigens or drug candidates) with relatively low solubility in water or aqueous solvents would be more easily coupled to microspheres if the coupling could be performed in alcoholic or dimethyl sulfoxide (DMSO) solvent.

SUMMARY OF THE INVENTION

The following description of various method and population embodiments is not to be construed in any way as limiting the subject matter of the appended claims.

One embodiment relates to a method for forming a dyed microsphere. The method includes activating a chemical structure coupled to a dye using heat or light to form a reaction intermediate in the presence of a microsphere. The reaction intermediate covalently attaches to a polymer of the microsphere thereby coupling the dye to the polymer and forming the dyed microsphere. Although the method is described herein with respect to one microsphere, it is to be understood that this method may be used to dye multiple microspheres simultaneously.

In one embodiment, activating the chemical structure includes heating the chemical structure coupled to the dye to a temperature of about 110° C. In another embodiment, activating the chemical structure includes heating the chemical structure coupled to the dye to a temperature of about 50° C. to about 80° C. Preferably, activating the chemical structure includes heating the chemical structure coupled to the dye to a temperature below the glass transition temperature of the polymer. The microsphere preferably has substantially the same shape before and after activation of the chemical structure. In addition, the dye preferably has the same structure and substantially the same composition before and after activation of the chemical structure.

Preferably, the chemical structure and the dye do not detach from the polymer when the dyed microsphere is disposed in an organic solvent. In one embodiment, the polymer consists essentially of polystyrene crosslinked with divinyl benzene. In other words, the polymer may be formed primarily of polystyrene crosslinked with divinyl benzene. The microspheres also may contain carboxyl groups or other appropriate groups such as aminos on the surfaces of the microspheres. These groups may be generated by including acrylic acid or methacrylic acid as monomers in the polymerization of the microspheres. In one example, about 1% to about 10% of the monomers involved in the polymerization may be surface-group-related monomers. Therefore, in one embodiment, the dyed microsphere includes one or more functional groups (e.g., carboxyl, amino, etc.) attached to, or synthesized on, the polymer such that one or more molecules can be attached to the dyed microsphere via the one or more functional groups.

In some embodiments, the chemical structure includes an aromatic sulfonyl azide. In another embodiment, the chemical structure includes 1,5-ethyl-di-amino-naphthalene-sulfonic azide. In an additional embodiment, the reaction intermediate includes a sulfonyl nitrene group. Alternatively, the reaction intermediate may include a carbene group or a benzophenone triplet.

In a further embodiment, the reaction intermediate includes a functional group separated from the dye by a non-activated portion of the chemical structure. In one such embodiment, the reaction intermediate includes a functional group located on one side of a non-activated portion of the chemical structure, and the dye is located on another side of the non-activated portion substantially opposite to the one side.

In some embodiments, the method includes activating an additional chemical structure coupled to an additional, different dye using heat or light to form a different reaction intermediate in the presence of the microsphere. The different reaction intermediate covalently attaches to the polymer of the microsphere thereby coupling the additional different dye to the polymer. In one such embodiment, the different dye has substantially the same structure and composition before and after activation of the additional chemical structure. This dye may be different from the other dye in chemical structure, excitation characteristics, emission characteristics, etc. The additional chemical structure used to couple the different dye to the polymer may be the same as or different than the chemical structure that is used to couple the other dye to the polymer. The two different dyes may be coupled to the polymer simultaneously or sequentially. In addition, the two different dyes may be coupled to the polymer of microspheres in different populations in different amounts, ratios, or concentrations. Each of the embodiments of the method described above may include any other step(s) described herein.

Another embodiment relates to a method for forming a dyed microsphere coupled to a molecule. This method includes activating a chemical structure coupled to a dye using heat or light to form a reaction intermediate in the presence of a microsphere. The reaction intermediate covalently attaches to a polymer of the microsphere thereby coupling the dye to the polymer and forming the dyed microsphere. This method also includes synthesizing the molecule on an outer surface of the dyed microsphere. Although the method is described herein with respect to one microsphere, it is to be understood that the method can also be used to thin multiple dyed microspheres simultaneously, each of which is coupled to at least one molecule. In addition, although the method is described herein with respect to one molecule, it is to be understood that the method may include coupling more than one different molecule (e.g., multiple, different biomolecules) to each of the dyed microspheres.

In one embodiment, synthesizing the molecule includes disposing the dyed microsphere in an organic solvent. Preferably, the dyed microsphere has substantially the same dye characteristics before and after the synthesis. In one embodiment, the molecule that is synthesized on the outer surface of the dyed microsphere is a biomolecule. In another embodiment, the molecule includes an oligonucleotide, a peptide, or an oligosaccharide. In other embodiments, the molecule that is synthesized on the outer surface of the dyed microsphere is an organic molecule (e.g., a drug candidate). In some embodiments, the molecule is substantially insoluble in aqueous solvents. In different embodiments, synthesizing the molecule includes disposing the dyed microsphere in an aqueous solvent.

In some embodiments, activating the chemical structure includes heating the chemical structure coupled to the dye to a temperature of about 110° C. In another embodiment, activating the chemical structure includes heating the chemical structure coupled to the dye to a temperature of about 50° C. to about 80° C. Preferably, activating the chemical structure includes heating the chemical structure coupled to the dye to a temperature below the glass transition temperature of the polymer. The microsphere preferably has substantially the same shape before and after activation of the chemical structure. In addition, the dye preferably has the same structure and substantially the same composition before and after activation of the chemical structure.

Preferably, the chemical structure and the dye do not detach from the polymer when the dyed microsphere is disposed in an organic solvent. In one embodiment, the polymer consists essentially of polystyrene crosslinked with divinyl benzene. In other words, the polymer may be formed primarily of polystyrene crosslinked with divinyl benzene. In one embodiment, the dyed microsphere includes one or more functional groups (e.g., carboxyl, amino, etc.) attached to the polymer such that one or more molecules can be attached to, or synthesized on, the dyed microsphere via the one or more functional groups.

In some embodiments, the chemical structure includes an aromatic sulfonyl azide. In another embodiment, the chemical structure includes 1,5-ethyl-di-amino-naphthalene-sulfonic azide. In an additional embodiment, the reaction intermediate includes a sulfonyl nitrene group. Alternatively, the reaction intermediate may include a carbene group or a benzophenone triplet.

In a further embodiment, the reaction intermediate includes a functional group separated from the dye by a non-activated portion of the chemical structure. In one such embodiment, the reaction intermediate includes a functional group located on one side of a non-activated portion of the chemical structure, and the dye is located on another side of the non-activated portion substantially opposite to the one side.

In some embodiments, the method includes activating an additional chemical structure coupled to an additional, different dye using heat or light to form a different reaction intermediate in the presence of the microsphere. The different reaction intermediate covalently attaches to the polymer of the microsphere thereby coupling the additional, different dye to the polymer. In one such embodiment, the different dye has substantially the same structure and composition before and after activation of the additional chemical structure. This dye may be different from the other dye in chemical structure, excitation characteristics, emission characteristics, etc. The additional chemical structure used to couple the additional, different dye to the polymer may be the same as or different than the chemical structure that is used to couple the other dye to the polymer. The two or more different dyes may be coupled to the polymer simultaneously or sequentially. In addition, the two or more different dyes may be coupled to the polymer of microspheres in different populations in different amounts, ratios, or concentrations. Each of the embodiments of the method described above may include any other step(s) described herein.

An additional embodiment relates to a population of dyed microspheres. Each of the dyed microspheres of the population includes a dye attached to a polymer of each of the dyed microspheres by a chemical structure. A coefficient of variation in dye characteristics of the population of dyed microspheres attributable to the dye is less than about 10%. In one embodiment, the coefficient of variation is a coefficient of variation in a signal emitted by each of the dyed microspheres upon excitation of each of the dyed microspheres. In another embodiment, an amount of the dye attached to the polymer of each of the dyed microspheres is substantially equal.

In some embodiments, each of the dyed microspheres of the population includes an additional, different dye attached to the polymer of each of the dyed microspheres by an additional chemical structure. In one such embodiment, the coefficient of variation in the dye characteristics of the population of dyed microspheres attributable to the additional, different dye is less than about 10%. The two different dyes may be coupled to the polymer of microspheres in different populations in different amounts, ratios, or concentrations. In another embodiment, each of the dyed microspheres of the population includes a biomolecule synthesized on an outer surface of each of the dyed microspheres. In a different embodiment, each of the dyed microspheres of the population includes an organic molecule synthesized on an outer surface of each of the dyed microspheres.

In an additional embodiment, each of the dyed microspheres has substantially the same shape before and after the dye is attached to the polymer. In another embodiment, the dye has substantially the same structure and substantially the same composition before and after the dye is attached to the polymer. In a further embodiment, the chemical structure and the dye do not detach from the polymer when the population of dyed microspheres is disposed in an organic solvent.

In one embodiment, the polymer consists essentially of polystyrene crosslinked with divinyl benzene. In addition, each of the dyed microspheres may also include one or more functional groups attached to the polymer such that one or more molecules can be attached to each of the dyed microspheres via the one or more functional groups. In some embodiments, the chemical structure includes an aromatic sulfonyl azide. In another embodiment, the chemical structure includes 1,5-ethyl-di-amino-naphthalene-sulfonic azide. Each of the embodiments of the population of dyed microspheres may be further configured, composed, and/or formed as described herein. In addition, multiple populations configured as described above, but with different amounts, ratios, or concentrations of one or more dyes such that different populations can be distinguished from one another by their fluorescence characteristics (e.g., fluorescence wavelength(s), fluorescence intensity or intensities, or ratio of fluorescence intensities), may be included in a set for applications such as multiplexed analysis of a sample for multiple analytes of interest.

BRIEF DESCRIPTION OF THE DRAWINGS

Other objects and advantages of the invention will become apparent upon reading the following detailed description and upon reference to the accompanying drawings in which.

Figure 1:
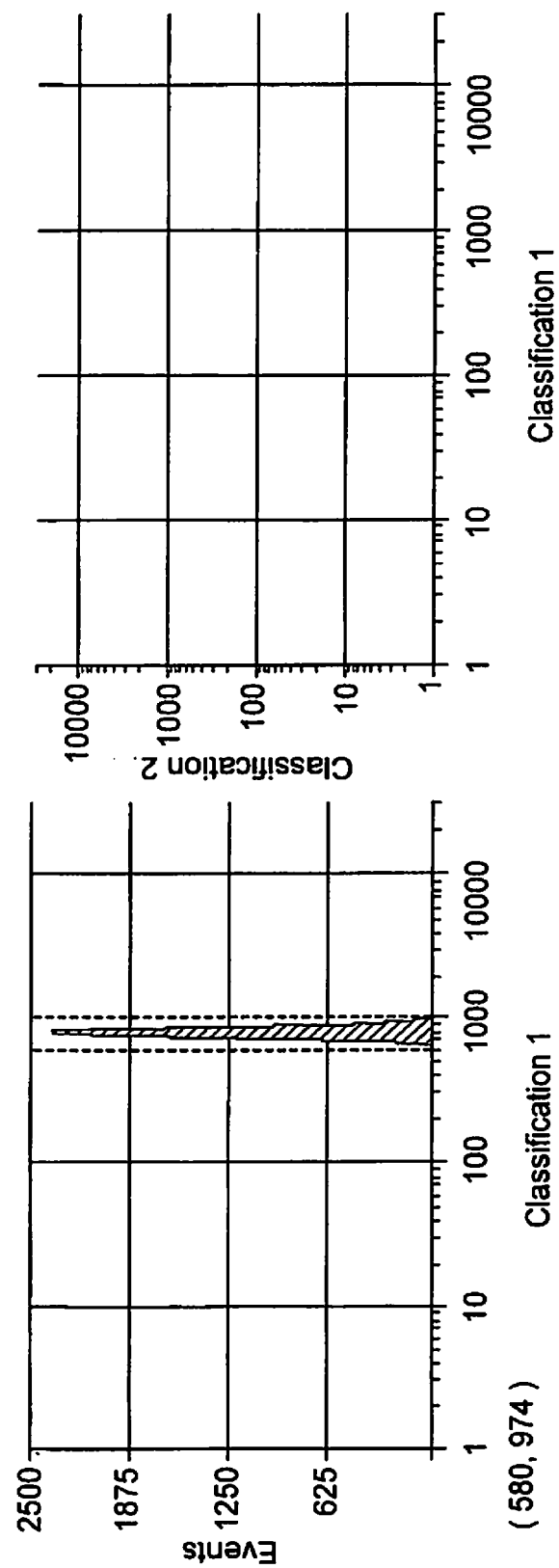
FIG. 1 is a plot of signals generated by classification channel 1 (CL1)/classification channel 2 (CL2) of a Luminex100 system for microspheres dyed according to the method embodiments described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although method and population embodiments are described herein with respect to fluorescent dyes, it is to he understood that the methods and populations described herein can be used with or include any other molecule(s) known in the art (e.g., fluorophores) that can be used to impart one or more measurable, distinguishing characteristics to the microspheres. Furthermore, many different fluorescent dyes are known in the art, and the term "fluorescent dye" as used herein is intended to encompass all fluorescent dyes known in the art.

Although embodiments are described herein with respect to microspheres, it is to he understood that the embodiments can be used with or include any discrete substances (e.g., microspheres, beads, particles, etc.) known in the art that are formed of a material to which a reaction intermediate as described herein can be covalently bound.

In general, methods for producing organotolerant dyed microspheres are described herein. Microspheres are generally dyed with fluorescent dyes such that the microspheres exhibit selected fluorescent signatures (e.g., fluorescent wavelength(s), fluorescent intensity or intensities, ratio of fluorescent intensities, etc.) when exposed to an excitation source (e.g., laser illumination) in the Luminex100 instrument commercially available from Luminex Corporation, Austin, Tex., as well as other measurement instruments known in the art. In the methods described herein, the dye is coupled to a chemical structure that is activated by light or heat to generate a reaction intermediate that causes the chemical structure to covalently attach to a polymer (e.g., a polymer matrix) of the microsphere thereby attaching the dye to the polymer of the microsphere.

One embodiment of such a method includes activating a chemical structure coupled to a dye using heat or light to form a reaction intermediate in the presence of a microsphere. The chemical structure to which the dye is coupled may be located within the microsphere during activation of the chemical structure. The chemical structure and the dye coupled thereto may be integrated into the microsphere prior to activation of the chemical structure using any suitable method known in the art. The reaction intermediate covalently attaches to a polymer of the microsphere thereby coupling the dye to the polymer (via the chemical structure) and forming the dyed microsphere. In this manner, the dyed microsphere may contain a dye located with the microsphere (e.g., within a to polymer matrix of the microsphere) as opposed to a dye located on the surface of the dyed microsphere.

The method embodiments described herein, therefore, include using dye structures and dyeing procedures different than those currently in use. For example, the method embodiments include adding one or more dyes coupled to one or more chemical structures to swollen microspheres and then permanently trapping them in the microspheres by curing (e.g., by activating the chemical structure(s) thereby forming reaction intermediate(s) that react covalently with the polymer of the microspheres). Swelling the microspheres to incorporate the chemical structures and the dyes coupled thereto into the microspheres prior to activation of the chemical structures may be performed as described in U.S. Pat. Nos. 6,514,295 to Chandler et al., U.S. Pat. No. 6,599,331 to Chandler et al., and U.S. Pat. No. 6,632,526 to Chandler et al., which are incorporated by reference as if fully set forth herein.

As described above, sulfonyl azides have been used to covalently attach various dyes to natural and synthetic polymers (films or fibers). However, it has been discovered that these chemical structures can be used to provide a tight (i.e., low) coefficient of variation (% CV) for fluorescence signals emitted by microspheres of a population and that the low % CV is retained after chemical structure activation and reaction with the polymer using the method embodiments described herein. Such tight fluorescence % CV is advantageous particularly for applications such as multiplexed analysis of a sample for multiple analytes in which the % CV of the fluorescence emitted by the microspheres has a direct effect on the accuracy with which the population to which the microspheres belong and thereby the reactants on the microspheres can be identified (e.g., as the % CV decreases, the accuracy of microsphere classification increases). In addition, reducing the fluorescence % CV of the microspheres typically allows more microsphere populations to be used in a single assay or experiment since the classification space corresponding to any one population is smaller thereby allowing more microsphere populations to be included in the classification space.

Sulfonyl azide coupled to a dye may be activated such that the activated sulfonyl azide can react with the polymer of a microsphere thereby producing organotolerant bead sets (i.e., bead sets that do not exhibit a change in their fluorescent characteristics (e.g., fluorescent intensity) subsequent to exposure of the bead sets to an organic solvent or a solvent mixture containing an organic solvent) that are compatible with the Luminex100 system and other flow cytometer systems that are commercially available as well as any other measurement system that utilizes or is configured for measurements of microspheres. Therefore, one advantage of the method embodiments described herein is that microspheres dyed by the method embodiments will not exhibit a change in their fluorescent signatures (e.g., reduced fluorescence intensity) after being exposed to one or more organic solvents. In other words, the chemical structure and the dye coupled thereto do not detach from the polymer and migrate out of the microsphere when the dyed microsphere is disposed in an organic solvent or contacted with a solvent mixture containing an organic solvent.

The method embodiments described herein may also be performed using sulfonyl azides and other chemical structures that may be activated to generate other and/or additional reactive groups (other nitrenes, carbenes, etc.) as well as chemical structures that may be activated by thermal and/or photochemical activation. The ethyl-di-amino-naphthalene-sulfonic-acid (EDANS) group described herein may also be supplemented or replaced with other aromatic structures, which may alter the activation temperature of the chemical structure. In this manner, the chemical structure used in the methods described herein may include an aromatic sulfonyl azide, 1,5-ethyl-di-amino-naphthalene-sulfonic azide, or any other suitable chemical structure known in the art. In other words, the methods described herein can be used with chemical structures other than those containing the EDANS group. The method embodiments described herein may also be used in conjunction with other bead dyeing methods.

To be useful in dyeing microspheres, the following general guidelines may be used to select the chemical structures and parameters or conditions of the dyeing methods. For example, in order to obtain the selected fluorescent signature of the microsphere, the percent yield of dye attachment to the polymer of the microsphere is preferably substantially consistent and preferably high. To obtain a tight % CV for classification fluorescent signals emitted by microspheres of the same population (e.g., fluorescent signals that impart distinguishing measurable characteristics to the microspheres such that one population of microspheres can be distinguished from another population of microspheres), each of the chemical structures is preferably activated to substantially the same extent so that substantially uniform dyeing of the individual microspheres in a population is obtained after covalent attachment.

The chemical structures may also be selected such that during the activation step, all of the different chemical structures incorporated into the microspheres react with the polymer of the microspheres under substantially the same conditions and to substantially the same extent. In this manner, the characteristics of the dyed microspheres (e.g., their fluorescent signal) may be controlled relatively easily and accurately. The dye chromophores selected for use in the method embodiments described herein are preferably stable under the activation conditions (e.g., ultraviolet (UV) light may excessively or differentially photobleach some chromophores). The microspheres are also preferably stable under the activation conditions selected for use in the method embodiments described herein (e.g., overheating may cause the microspheres to melt and lose their spherical shape).

The interior of microspheres may be composed essentially of a polymer such as polystyrene crosslinked with divinyl benzene, which is a fairly inert substrate for covalent coupling. Therefore, the chemical structures may be selected such that the reaction intermediate is reactive enough to cause insertion of the chemical structure and the dye coupled thereto into C—H or C—C bonds of this and other polymers of microspheres. Furthermore, the carboxylates and/or other functional groups on the surface of the microspheres preferably remain available for coupling to biomolecules or other molecules (e.g., organic molecules, drug candidates, etc.) after dyeing of the microspheres.

The dyeing methods described herein may be performed using a chemical structure such as the sulfonyl azide form of 1,5-EDANS shown below.

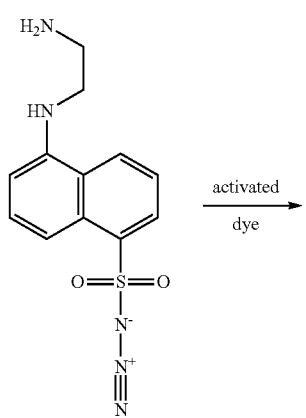

1,5-EDANS azide

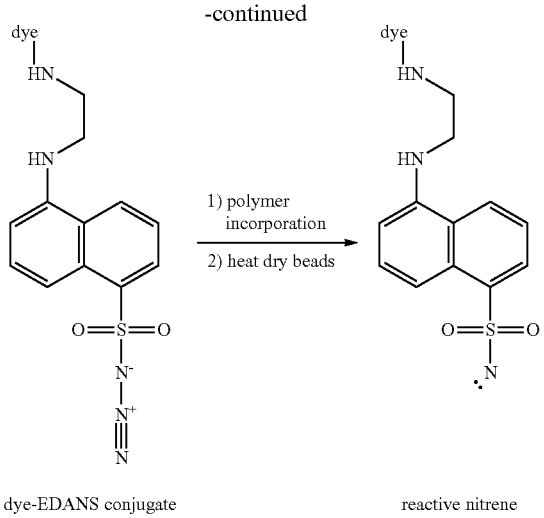

dye-EDANS conjugate    reactive nitrene

As shown in the first step of the above reaction, the free amino group on the 1,5-EDANS azide is used to couple the 1,5-EDANS azide to a dye molecule. The dye molecule may include any appropriate dye molecule known in the art. In one such example, the dye contains an amine reactive group such as a N-hydroxysuccinimide (NHS) ester group, isocyanate group, etc. that can be coupled to the free amino group on the 1,5-EDANS azide. Although in the example shown above one dye molecule is coupled to one chemical structure molecule, it is to be understood that chemical structures that allow more than one dye molecule to be coupled to each chemical structure molecule or more than one chemical structure to be coupled to each dye may be used in the embodiments described herein.

As shown in the second step of this reaction, the 1,5-EDANS azide coupled to the dye may be incorporated into the polymer of a microsphere (i.e., disposed within the polymer matrix of the microsphere). As further shown in this second step, heating the chemical structure incorporated into the polymer to a temperature of about 110° C. initiates a nitrogen extrusion reaction, which creates a reactive sulfonyl nitrene group on the 1,5-EDANS azide, which can form a covalent bond with the polymer of the microsphere. Therefore, activating the chemical structure may include heating the chemical structure coupled to the dye to a temperature of about 110° C.

Only substantially reactive intermediates can react with aliphatic C—H bonds such as those of polymeric microspheres. Examples of such highly reactive intermediates include carbenes, nitrenes, and benzophenone triplets. (See, for example, Molecular Probes Handbook of Fluorescent Probes and Research Products, Ninth edition, R. P. Haugland, Ed. sec 5.3, which is incorporated by reference as if fully set forth herein.) Therefore, the reaction intermediate that is formed during the method may include a nitrene group, a carbene group, a benzophenone triplet, or any other suitable functional group known in the art. It is noted that benzophenone can only be activated with UV light.

Most nitrenes and carbenes undergo relatively rapid unimolecular rearrangement reactions, which produce species that are less reactive than their nitrene and carbene counterparts. Therefore, such reaction intermediates are preferably formed in the presence of the microsphere(s) to be dyed (e.g., after incorporation into the microspheres) such that these groups can react with the polymer of the microsphere(s) before the unimolecular reactions occur. Sulfonyl azides, however, do not undergo a unimolecular rearrangement reaction and are, therefore, essentially "forced" to react with a molecule such as a polymer of a microsphere in the presence of the sylfonyl azides.

Using such chemical structures in the method embodiments described herein has a number of advantages over previously used dyeing methods and previously used dyes. For instance, the reactive group generated on the chemical structure by activation in the embodiments described herein is not part of the dye chromaphore. Therefore, the reactivity of the reactive group may be independent of the structure of the appended dye thereby increasing the number and types of fluorescent dyes that can be used to form organotolerant dyed microspheres. In addition, the reactive group can be incorporated into a chemical structure that may be coupled to many different dyes without designing a new synthesis for each dye. In addition, the 1,5 substituted naphthalene core allows the reactive sulfonyl nitrene to be positioned away from (i.e., spaced from) the dye molecule thereby reducing, and perhaps minimizing, the chance that the nitrene will react with the appended dye instead of a polymer strand of the microsphere. In this manner, the reaction intermediate may include a functional group separated from the dye by a non-activated portion of the chemical structure. In some embodiments, the reaction intermediate includes a functional group located on one side of a non-activated portion of the chemical structure. The dye may be located on another side of the non-activated portion substantially opposite to the one side.

Furthermore, the intermediate nitrene can be generated by heating the chemical structure to a temperature of greater than or equal to about 110° C., which is substantially below both the glass transition temperature of polymers of currently used microspheres and the decomposition temperature of currently used dyes. Therefore, in one embodiment, activating the chemical structure includes heating the chemical structure coupled to the dye to a temperature below the glass transition temperature of the polymer. As such, the microsphere(s) being dyed will have substantially the same shape (e.g., spherical shape) before and after activation of the chemical structure.

Structure-reactivity relationships and their influence on covalent dyeing may be investigated for the development of ideal reactive dyes (i.e., a chemical structure coupled to a dye). For example, altering the sulfonyl azide aromatic ring may provide chemical structures that react at lower temperatures with minimal spectral interference in the measurements to be performed on the dyed microspheres. In one particular example, additional substitution to the naphthalene ring may reduce the reaction temperature to a reaction temperature that may be ideal for the embodiments described herein (e.g., a reaction temperature of about 50° C. to about 80° C.). In this manner, activating the chemical structure may including heating the chemical structure coupled to the dye to a temperature of about 50° C. to about 80° C. In addition, modeling of reactions may be performed to determine the modes of reaction of sulfonyl azide (not all reactions may lead to covalent attachment). For example, a solution of azide may be heated in toluene solution (a simple model of polystyrene), and the products may be isolated and characterized.

The scheme below outlines a synthetic reaction that was used to produce a chemical structure coupled to a dye that is useful in methods described herein.

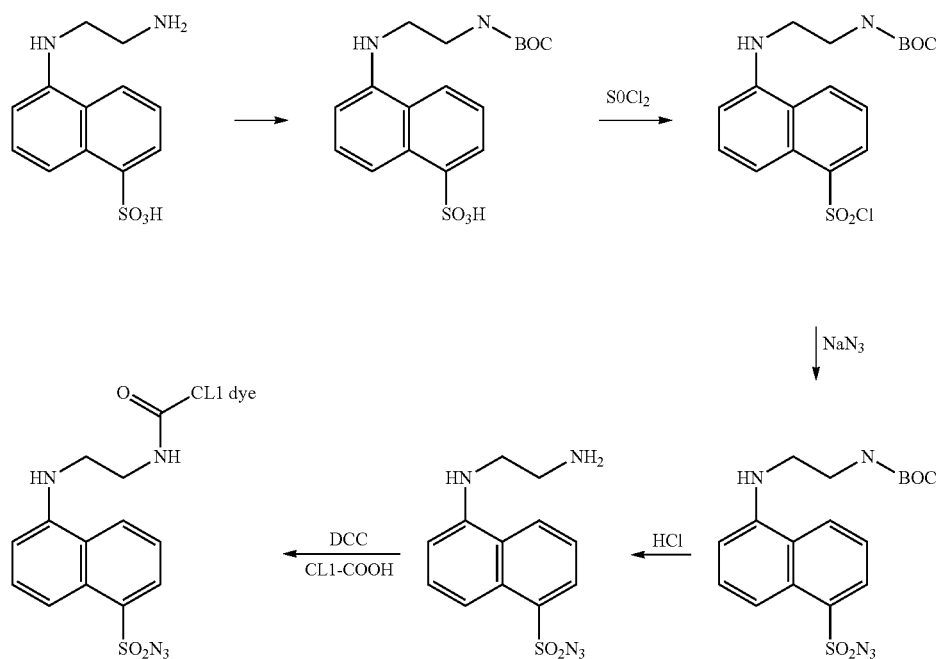

The reaction shown above produces a sulfonyl azide coupled to a dye. The dye molecule in this example is a dye molecule that upon excitation will emit fluorescence of a wavelength or wavelengths in the detection window of classification channel 1 (CL1) of the Luminex100 system. However, any suitable dye known in the art may be coupled to the chemical structure as shown above. Although in the example shown above one dye molecule is coupled to one chemical structure molecule, it is to be understood that chemical structures that allow more than one dye molecule to be coupled to each chemical structure molecule or more than one chemical structure to be coupled to each dye may be used in the embodiments described herein.

Microspheres were dyed with the sulfonyl azide coupled dye produced by the above reaction as described herein. After heating, the unreacted dye was washed out of the microspheres with tetrahydrofuran (THF) and methanol. Washing of the microspheres may be performed using any appropriate method known in the art. The resulting CL1/classification channel 2 (CL2) scatterplot of the dyed microspheres measured with a Luminex100 system is shown in FIG. 1. As shown in FIG. 1, the results of this experiment illustrate that an aromatic sulfonyl azide can be used to attach a fluorescent dye to polystyrene polymer by simple heating of dried microspheres into which the aromatic sulfonyl azide coupled dye has been incorporated. The resulting bead population had a % CV for CL1 of 8%.

In some embodiments, the dyeing methods described above include activating an additional chemical structure coupled to an additional, different dye using heat or light to faun a different reaction intermediate in the presence of the microsphere(s). The different reaction intermediate covalently attaches to the polymer of the microsphere(s) thereby coupling the additional, different dye to the polymer. The additional chemical structure may be the same as or different than the chemical structure coupled to the other dye. For example, both dyes may be coupled to 1,5-ethyl-di-amino-naphthalene-sulfonic azide molecules. Alternatively, the different dyes may be coupled to different aromatic sulfonyl azides. The additional, different dye preferably has substantially the same structure and composition before and after activation of the chemical structure. In this manner, activation of the chemical structure and attachment of the chemical structure to the microsphere will not alter the dye. The two different dyes may he coupled to the polymer simultaneously or sequentially. In addition, the two different dyes may be coupled to the polymer of microspheres in different populations in different amounts, ratios, or concentrations. Furthermore, more than two different dyes may be coupled to a microsphere using the methods described herein.

Organotolerant beads produced by the method embodiments described herein having oligosequences covalently coupled to a surface of the microspheres may be of immense interest for applications such as multiplexed hybridization assays. In particular, the oligonucleotides may be synthesized directly (and possibly automatically) on the organotolerant dyed microspheres. Direct (and optionally automatic) oligo-synthesis on fluorescent microspheres will reduce the cost of producing nucleotide-coupled microspheres compared to currently used methods for producing such microspheres that include synthesizing the oligonucleotides on a DNA synthesis resin, "detaching" the oligonucleotides from the DNA synthesis resin, and then "attaching" the oligonucleotides to fluorescent dyed microspheres. The oligonucleotides may be synthesized on the surface of the microspheres formed according to the method embodiments described herein (e.g., via a functional group on the surface of the microspheres) using any appropriate oligonucleotide synthesis method known in the art.

In one embodiment, therefore, the method includes synthesizing a molecule on an outer surface of the microsphere(s) after the microsphere(s) have been dyed as described above. In some embodiments, synthesizing the molecule includes disposing the dyed microsphere in an organic solvent or a solvent mixture containing an organic solvent. Unlike other dyed microspheres, the microspheres described herein will not lose their dye characteristics when disposed in an organic solvent. As such, the dyed microspheres will have substantially the same dye characteristics before and after the synthesis. The molecule synthesized on the microsphere(s) may be a biomolecule. For example, the biomolecule may be any biomolecule with relatively low water solubility known in the art that can be more easily attached to fluorescent microspheres if the attachment reaction can be carried out in an organic solvent. In addition, the molecule may include an oligonucleotide, a peptide, or an oligosaccharide. The oligonucleotide, the peptide, and the oligosaccharide synthesized on the microsphere(s) may include any appropriate such molecules known in the art.

In another embodiment, the molecule may include an organic molecule (e.g., a drug candidate). Accordingly, successful reagents for genomics based drug discovery can be generated using the covalently dyed microspheres described herein. In some embodiments, the molecule includes any molecule that is substantially insoluble in aqueous solvents.

Alternatively, synthesis of the molecule may include disposing the dyed microsphere in an aqueous solvent. In this manner, molecules may be synthesized on the microspheres dyed as described herein in both aqueous and organic solvents thereby substantially increasing the usefulness of the microspheres. Obviously, pre-synthesized molecules may also be attached to the dyed microspheres described herein using any appropriate method known in the art.

Another embodiment relates to a population of dyed microspheres. Each of the dyed microspheres of the population includes a dye attached to a polymer of each of the dyed microspheres by a chemical structure. The dye and the chemical structure may include any of the dyes and chemical structures described herein. A coefficient of variation in dye characteristics of the population of dyed microspheres attributable to the dye is less than about 10%. The coefficient of variation may be a coefficient of variation in a signal (e.g., a fluorescence intensity) emitted by each of the dyed microspheres in the population upon excitation of each of the dyed microspheres. In this manner, the coefficient of variation may be a coefficient of variation in the classification signal of the dyed microspheres. The dye may be coupled to polymer of microspheres in different populations in different amounts or concentrations.

In one embodiment, an amount of the dye attached to the polymer of each of the dyed microspheres is substantially equal. In some embodiments, each of the dyed microspheres of the population also includes an additional, different dye attached to the polymer of each of the dyed microspheres by an additional chemical structure. In one such embodiment, the coefficient of variation in the dye characteristics of the population of dyed microspheres attributable to the additional, different dye is less than about 10%. The two different dyes may be coupled to the polymer of microspheres in different populations in different amounts, ratios, or concentrations. In addition, more than two different dyes may be coupled to the polymer of microspheres in different populations in different amounts, ratios, or concentrations.

Each of the dyed microspheres preferably has substantially the same shape before and after the dye is attached to the polymer. In addition, the dye has substantially the same structure and substantially the same composition before and after the dye is attached to the polymer. Preferably, the chemical structure and the dye do not detach from the polymer when the population of dyed microspheres is disposed in an organic solvent. The chemical structure may include an aromatic sulfonyl azide. In one embodiment, the chemical structure includes 1,5-ethyl-di-amino-naphthalene-sulfonic azide. However, the chemical structure may include any other chemical structures described herein.

The polymer may consist essentially of polystyrene crosslinked with divinyl benzene. The polymer of the microspheres may also or alternatively include any other appropriate polymer known in the art. The microspheres also may contain carboxyl groups or other appropriate groups such as aminos on the surfaces of the microspheres. These groups may be formed on the surfaces of the microspheres by including acrylic acid or methacrylic acid as monomers in the polymerization of the microspheres. In one example, about 1% to about 10% of the monomers involved in the polymerization may be surface-group-related monomers. Therefore, in one embodiment, the dyed microsphere includes one or more functional groups (e.g., carboxyl, amino, etc.) attached to the polymer such that one or more molecules can be attached to the dyed microsphere via the one or more functional groups.

In some embodiments, each of the dyed microspheres of the population includes a biomolecule synthesized on an outer surface of each of the dyed microspheres. The biomolecule may include any of the biomolecules described herein. In other embodiments, each of the dyed microspheres of the population includes an organic molecule synthesized on an outer surface of each of the dyed microspheres. The organic molecule may include any organic molecule described herein. Each of the embodiments of the population of dyed microspheres described herein may be further configured, composed, and/or formed as described herein. In addition, the embodiments of the population of dyed microspheres described above have all of the advantages of the method embodiments described herein.

The following examples are not to be construed as limiting embodiments of the invention and are included herein for example purposes only. All of the reagents described in the followings examples were purchased from Sigma-Aldrich (unless otherwise noted) and were used as received.

EXAMPLE 1

N-(ζ-carboxyhexyl)-2,3,3-trimethylindolinium iodide

To 2.45 g of 2,3,3-trimethylindolenine (15.4 mmole) in 20 mL of acetonitrile was added 3.00 g of 6-bromohexanoic acid (15.4 mmole), and the solution was heated under reflux for 14 hours. After concentration in vacuo, the residue was taken up in 100 mL of deionized water and 25 mL of ethyl acetate. The aqueous portion was washed 2 additional times with 25 mL of ethyl acetate. After concentration in vacuo of the aqueous portion, 50 mL of dry diethyl ether was added to the residue. After 2 days at 4° C., 1.62 g (30%) of N-(ζ-carboxyhexyl)-2,3,3-trimethylindolinium iodide as a purple solid was obtained by filtration.

EXAMPLE 2

2,4-bis [N-(ζ-carboxyhexyl)-1,3,3-trimethyl-2-indolinylidene-methyl]cylclobutenediylium-1,3-diolate A solution of 0.80 g (2.25 mmole) N-(ζ-carboxyhexyl)-2,3,3-trimethylindolinium iodide (prepared in Example 1) and 0.13 g (1.12 mmole) 3,4-dihydroxy-3-cyclobutene-1,2-dione in 25 mL of toluene and 25 mL of butanol was refluxed with a Dean-Stark trap for 15 hours. The solution was concentrated in vacuo, and the residue was charged onto a silica gel column slurry packed with chloroform eluted with 0-5% methanol in chloroform. Concentration in vacuo of the blue fraction gave a blue oil. The blue oil was dissolved in 10 mL of absolute ethanol and concentrated in vacua to give 0.44 g (31%) of a gold-metallic colored solid.

EXAMPLE 3 tert-butoxycarbonyl (t-BOC) protected 1,5-EDANS

To 1.98 g of 5-(2-aminoethylamino)-1-naphthalene-sulfonic acid (1,5-EDANS, 7.42 mmole) and 2.78 g of sodium bicarbonate (33.0 mmole) in 50 mL of methanol was added 3.59 g of di-tert-butyldicarbonate (16.4 mmole) and mixed by a bath sonicator for 5 hr. After filtration, the solution was concentrated in vacuo, and the residue was triturated with 20 mL of hexane to give, after filtration, 2.92 g of t-BOC protected 1,5-EDANS as a tan solid.

EXAMPLE 4 t-BOC protected 1,5-EDANS azide

To 10 mL of deionized water was added 1.55 g (4.0 mmole) of t-BOC protected-1,5-EDANS (prepared in Example 3). After all of the solids were dissolved, 2.7 mL (4.1 mmole) of a 40% solution of tetrabutylammonium hydroxide was added. The mixture was extracted with chloroform, dried with magnesium sulfate (anhydrous), and concentrated in vacuo to a crystallizing foam. To the foam, dissolved in 100 mL of chloroform, was added 120 µL of dimethylformamide and 4 mL of thionyl chloride. After 3.5 hours of reflux, the solution was poured over 20 g of water ice and 10 mL of ammonium chloride (saturated). The resulting solution was quickly extracted into chloroform, dried over magnesium sulfate (anhydrous), and concentrated in vacuo to 2.67 g of crude t-BOC protected 1,5-EDANS chloride, a dark yellow oil which was used immediately without further purification.

To the yellow oil, dissolved in 22 mL of dimethylformamide, was added dropwise over 5 minutes a solution made from 0.38 g (5.8 mmole) of sodium azide and 1 mL of deionized water. After stirring at room temperature for 21.5 hours, the solution was concentrated in vacuo, taken up into 50 mL of chloroform, washed with deionized water, dried with anhydrous magnesium sulfate and concentrated in vacuo to 0.68 g (43%) of t-BOC protected 1,5-EDANS azide.

EXAMPLE 5

1,5-EDANS azide

To 0.2 g (0.51 mmole) of t-BOC protected 1,5-EDANS azide (prepared in Example 4) in 10 mL of methylene chloride at 0° C. was added dropwise over 5 minutes 65 µL of trifluoroacedic acid in 1 mL of methylene chloride at 0° C. The stirred solution was warmed to room temperature for 16 hours and to reflux for 1 hour. The solution was diluted with 40 mL of methylene chloride and washed four times with 10 mL of saturated sodium bicarbonate and concentrated in vacuo to 0.16 g of 1,5-EDANS azide as a yellow oil.

EXAMPLE 6

To 12 mg (0.04 mmole) of 1,5-EDANS azide (prepared in Example 5) and 13 mg (0.02 mmole) of 2,4-bis [N-(ζ-carboxyhexyl)-1,3,3-trimethyl-2-indolinylidene-methyl]cylclobetenediylium-1,3-diolate (prepared in Example 2) in 2 mL of chloroform was added 18 mg (0.09 mmole) of dicyclohexylcarbodiimide and 3.5 mg of 1-hydroxybenzotriazole. After stirring for 15 hours, the solution was filtered, and the filtrate was concentrated in vacuo to a blue residue, which was used without further purification.

EXAMPLE 7

Organotolerant Microspheres

Carboxylated, crosslinked polystyrene microspheres (diameter 5.6 µm, available from Polymer Laboratories, Ltd., Shropshire, United Kingdom, or Bangs Laboratories, Inc., Fishers, Ind.) were impregnated with the blue residue from Example 6 using the procedure described in U.S. Pat. No. 6,514,295 to Chandler et al., U.S. Pat. No. 6,599,331 to Chandler et al., and U.S. Pat. No. 6,632,526 to Chandler et al., which are incorporated by reference as if fully set forth herein.

A dispersion of the dyed microspheres in methanol were placed in a 5 mL conical flask and concentrated in vacuo. The microspheres under a nitrogen atmosphere were heated in an oil bath at 110° C. for 13 hours. The microspheres were washed three times with tetrahydrofuran, one time with methanol, and one time with deionized water. The wash solvents were removed by centrifugation and decantation. The microspheres were finally dispersed in deionized water for storage and testing.

Figure 2:
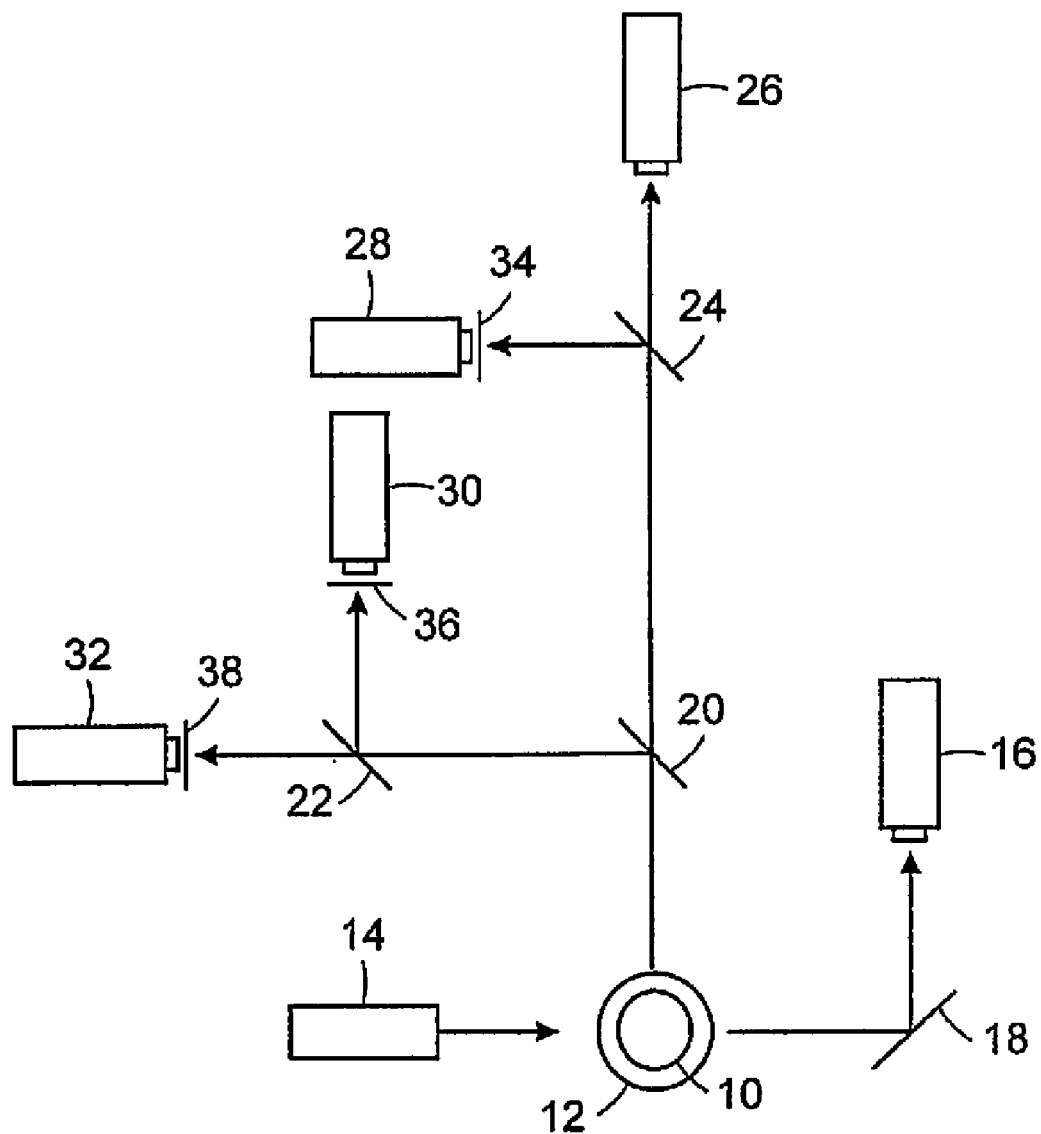
FIG. 2 is a schematic diagram illustrating one example of a measurement system that may be used to perform experiments using microspheres and microsphere populations formed according to the method embodiments described herein.

FIG. 2 illustrates one example of a measurement system that may be used to perform in experiments with the dyed microspheres described herein. It is noted that FIG. 2 is not drawn to scale. In particular, the scale of some of the elements of the figure are greatly exaggerated to emphasize characteristics of the elements. Some elements of the measurement system such as a digital signal processor (DSP) have not been included in the figure for the sake of clarity.

In FIG. 2, the measurement system is shown along a plane through the cross-section of cuvette 12 through which microspheres 10 flow. Microspheres 10 are microspheres dyed according to the embodiments described herein. In one example, the cuvette may be a standard quartz cuvette such as that used in standard flow cytometers. Any other suitable type of viewing or delivery chamber, however, may also be used to deliver the sample for analysis.

The measurement system includes light source 14. Light source 14 may include any appropriate light source known in the art such as a laser. The light source may be configured to emit light having one or more wavelengths such as blue light or green light. Light source 14 may be configured to illuminate the microspheres as they flow through the cuvette. The illumination may cause the microspheres to emit fluorescent light having one or more wavelengths or wavelength bands. In some embodiments, the system may include one or more lenses (not shown) configured to focus light from the light source onto the microspheres or the flowpath. The system may also include more than one light source (not shown). In one embodiment, the light sources may be configured to illuminate the microspheres with light having different wavelengths (e.g., blue light and green light). In some embodiments, the light sources may be configured to illuminate the microspheres at different directions.

Light scattered forwardly from the microspheres may be directed to detection system 16 by folding mirror 18 or another such light directing component. Alternatively, detection system 16 may be placed directly in the path of the forwardly scattered light. In this manner, the folding mirror or other light directing components may not be included in the system. In one embodiment, the forwardly scattered light may be light scattered by the microspheres at an angle of about 180 degrees from the direction of illumination by light source 14, as shown in FIG. 2. The angle of the forwardly scattered light may not be exactly 180 degrees from the direction of illumination by the light source such that incident light from the light source may not impinge upon the photosensitive surface of the detection system. For example, the forwardly scattered light may be light scattered by the microspheres at angles less than or greater than 180 degrees from the direction of illumination (e.g., light scattered at an angle of about 170 degrees, about 175 degrees, about 185 degrees, or about 190 degrees).

Light scattered and/or emitted by the microspheres at an angle of about 90 degrees from the direction of illumination by the light source may also be collected. In one embodiment, this scattered light may be separated into more than one beam of light by one or more beamsplitters or dichroic mirrors. For example, light scattered at an angle of about 90 degrees to the direction of illumination may be separated into two different beams of light by beamsplitter 20. The two different beams of light may be separated again by beamsplitters 22 and 24 to produce four different beams of light. Each of the beams of light may be directed to a different detection system, which may include one or more detectors. For example, one of the four beams of light may be directed to detection system 26. Detection system 26 may be configured to detect light scattered by the microspheres.

The other three beams of light may be directed to detection systems 28, 30, and 32. Detection systems 28, 30, and 32 may be configured to detect fluorescence emitted by the microspheres. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence.

In some embodiments, spectral filters 34, 36, and 38 may be coupled to detection systems 28, 30, and 32, respectively. The spectral filters may be configured to block fluorescence of wavelengths other than that which the detection systems are configured to detect. In addition, one or more lenses (not shown) may be optically coupled to each of the detection systems. The lenses may be configured to focus the scattered light or emitted fluorescence onto a photosensitive surface of the detectors.

The detector's output current is proportional to the fluorescent light impinging on it and results in a current pulse. The current pulse may be converted to a voltage pulse, low pass filtered, and then digitized by an A/D converter. A DSP integrates the area under the pulse to provide a number which represents the magnitude of the fluorescence.

In some embodiments, the output signals generated from fluorescence emitted by the microspheres may be processed to determine an identity of the microspheres and information about a reaction taking place on the surface of the microspheres. For example, two of the output signals may be used to determine an identity of the microspheres, and the other output signals may be used to determine a reaction taking place on the surface of the microspheres.

Although the system of FIG. 2 is shown to include two detection systems having two different detection windows for distinguishing between microspheres, having different dye characteristics, it is to be understood that the system may include more than two such detection windows (i.e., 3 detection windows, 4 detection windows, etc.). In such embodiments, the system may include additional beamsplitters and additional detection systems having other detection windows.

In addition, spectral filters and/or lenses may be coupled to each of the additional detection systems.

In another embodiment, the system may include two or more detection systems configured to distinguish between different materials that are reacted on the surface of the microspheres. The different reactant materials preferably have dye characteristics that are different than the dye characteristics of the microspheres.

Additional examples of measurement systems that may be used to perform measurements on the dyed microspheres described herein are illustrated in U.S. Pat. No. 5,981,180 to Chandler et al., U.S. Pat. No. 6,046,807 to Chandler, U.S. Pat. No. 6,139,800 to Chandler, U.S. Pat. No. 6,366,354 B1 to Chandler, U.S. Pat. No. 6,411,904 B1 to Chandler, U.S. Pat. No. 6,449,562 B1 to Chandler et al., and U.S. Pat. No. 6,524,793 B1 to Chandler et al., which are incorporated by reference as if fully set forth herein. The measurement system described herein may also be further configured as described in these patents. In addition, the assays and the experiments in which the dyed microsphere and population embodiments described herein may be used include any of the assays and experiments described in these patents and any other assays and experiments known in the art.

It will be appreciated to those skilled in the art having the benefit of this disclosure that this invention is believed to provide methods for forming dyed microspheres and populations of dyed microspheres. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A compound having the formula:

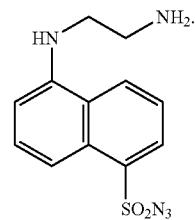

2. A composition comprising 1,5-ethyl-di-amino-naphthalene-sulfonic azide attached to a dye.

3. The composition of claim 2, further comprising a polymer attached to the 1,5-ethyl-di-amino-naphthalene-sulfonic azide.

4. A population of dyed microspheres, wherein each of the dyed microspheres of the population comprises a dye attached to a polymer of each of the dyed microspheres by a chemical structure in the interior of each of the dyed microspheres, and wherein a coefficient of variation in dye characteristics of the population of dyed microspheres attributable to the dye is less than about 10% and wherein the chemical structure comprises 1,5-ethyl-di-amino-napthalene-sulfonic azide.

5. The population of claim 4, wherein the coefficient of variation is a coefficient of variation in a signal emitted by each of the dyed microspheres upon excitation of each of the dyed microspheres.

6. The population of claim 4, wherein an amount of the dye attached to the polymer of each of the dyed microspheres is substantially equal.

7. The population of claim 4, wherein each of the dyed microspheres of the population further comprises an additional, different dye attached to the polymer of each of the dyed microspheres by an additional chemical structure.

8. The population of claim 7, wherein the coefficient of variation in the dye characteristics of the population of dyed microspheres attributable to the additional, different dye is less than about 10%.

9. The population of claim 4, wherein each of the dyed microspheres of the population further comprises a biomolecule synthesized on an outer surface of each of the dyed microspheres.

10. The population of claim 4, wherein each of the dyed microspheres of the population further comprises an organic molecule synthesized on an outer surface of each of the dyed microspheres.

11. The population of claim 4, wherein each of the dyed microspheres has substantially the same shape before and after the dye is attached to the polymer.

12. The population of claim 4, wherein the dye has substantially the same structure and substantially the same composition before and after the dye is attached to the polymer.

13. The population of claim 4, wherein the chemical structure and the dye do not detach from the polymer when the population of dyed microspheres is disposed in an organic solvent.

14. The population of claim 4, wherein the polymer consists essentially of polystyrene crosslinked with divinyl benzene.

15. The population of claim 4, wherein each of the dyed microspheres further comprises one or more functional groups attached to the polymer of each of the dyed microspheres such that one or more molecules can be attached to each of the dyed microspheres via the one or more functional groups.

* * * * *